United States Patent [19]
Lehtinen et al.

[11] Patent Number: 4,574,624
[45] Date of Patent: Mar. 11, 1986

[54] ULTRASONIC ECHO SOUNDING DEVICE FOR OBSERVING WEB FORMATION AND PULP SUSPENSION FLOW IN A PAPER MACHINE

[75] Inventors: Antti Lehtinen, Jyväskylä; Seppo Lepistö, Palokka, both of Finland

[73] Assignee: Valmet Oy, Finland

[21] Appl. No.: 623,363

[22] Filed: Jun. 22, 1984

[30] Foreign Application Priority Data

Jul. 6, 1983 [FI] Finland .................. 832483

[51] Int. Cl.$^4$ ............... G01N 11/00; G01N 29/02
[52] U.S. Cl. .................. 73/63; 73/61 R; 73/629; 73/642; 162/198
[58] Field of Search .............. 73/63, 61 R, 584, 629, 73/642; 162/198

[56] References Cited

U.S. PATENT DOCUMENTS

| | | | |
|---|---|---|---|
| 3,442,756 | 5/1969 | Lehtinen | 162/198 |
| 4,381,674 | 5/1983 | Abts | 73/61 R |
| 4,412,451 | 11/1983 | Uusitalo et al. | 73/61 R |
| 4,509,360 | 4/1985 | Erwin | 73/61 R |

FOREIGN PATENT DOCUMENTS 275499  3/1969  U.S.S.R. .................. 73/63

*Primary Examiner*—Howard A. Birmiel
*Attorney, Agent, or Firm*—Steinberg & Raskin

[57] ABSTRACT

An ultrasonic echo sounding device permits observation of the web formation and/or the pulp suspension flow on the wire part and in the head box of a paper machine. The device includes a series of ultrasonic detectors connected to the wall of the flow channel in the head box and/or to the forming wire. The detectors direct an ultrasonic field at the pulp suspension layer, and the echo signals received from the pulp suspension layer are detected. The detectors operate as acoustic lenses so that the focal points thereof are located in the transverse direction of the pulp suspension flow and in the direction of thickness of the pulp suspension layer in a manner whereby information concerning fibre bundles, air bubbles, variations in consistency, corresponding parameters and their variations in the transverse direction of the pulp suspension flow and in the direction of thickness of the pulp suspension layer are indicated by the device.

22 Claims, 2 Drawing Figures

ULTRASONIC ECHO SOUNDING DEVICE FOR OBSERVING WEB FORMATION AND PULP SUSPENSION FLOW IN A PAPER MACHINE

BACKGROUND OF THE INVENTION

The present invention relates to an ultrasonic echo sounding device for the observation of the web formation and/or pulp suspension flow on the wire part in the head box of a paper machine. More particularly, the invention relates to a device having a series of ultrasonic detectors connected to the wall of the flow channel in the head box and/or to the forming wire or wires. The detectors direct an ultrasonic field at the pulp suspension and the echo signals received from the pulp suspension are detected.

Known prior art devices measure the thickness of a pulp layer placed on the wire in the wire part of a paper machine by an ultrasonic echo method. This is accomplished by placing a detector crystal beneath the wire, whereas the water film at the bottom surface of the wire acts as the generator of the acoustic contact. This prior art techinque is disclosed in Finnish Pat. Nos. 35,621 and 35,622 of the present inventor.

Acoustic microscopes based on so-called acoustic lenses are known in the prior art. The construction and principle of operation of such microscopes are described in a paper in *Scientific American,* Oct. 1979, entitled "The Acoustic Microscope", by Calvin F. Quate, pages 58 to 65.

SUMMARY OF THE INVENTION

The principal object of the present invention is to provide an ultrasonic echo sounding device for obtaining information concerning, for example, the pulp suspension flowing in the head box or the pulp suspension layer formed on the wire or between two wires.

The control of the web formation in a paper machine is decisively important in view of the properties and the quality of the paper being produced. The web formation is partly based on the pulp suspension flow passing through the head box. Some important parameters affecting the formation of the web are the consistency of the pulp and its distribution in the direction of thickness of the pulp suspension layer, the air bubbles included in the pulp suspension layer, and the overall air content. It is also important to know the quantity and the size distribution of fibre bundles or flocs at different positions in the pulp suspension flow or layer.

The device of the invention, as well as uses of same, provide a greater quantity of more usable information than the devices of the prior art concerning the pulp suspension flow and/or the pulp suspension layer from which the fibre web is formed on a wire or between two wires.

Present day printing methods and printing machines impose ever higher requirements on the paper, especially on its structure and its surface properties. The device of the present invention is an efficient tool for modern development of paper by means of which an abundance of accurate information is obtained concerning the pulp suspension flows and the various stages of the web formation and their different parameters.

In order to achieve the aforementioned objectives as well as future objectives, the device of the invention includes a detector arrangement having a series of detectors. The detector arrangement operates on the principle of acoustic lenses, with the focal point of the detector or the focal points of the different detectors of a series of detectors located in the transverse direction of the pulp suspension flow and/or in the direction of thickness of the pulp suspension layer. The detectors are located in a manner whereby information is received concerning fibre bundles, air bubbles, variations in consistency, or on corresponding parameters and on their variations in the substantially lateral direction of the pulp suspension flow and/or in the direction of thickness of the pulp suspension layer.

Furthermore, the device of the invention comprises a series of ultrasonic detectors, each of which has a focal distance different in length from the other detectors, pulse generators connected to the detectors, a microprocessor unit, a sequence generator which controls the pulse generators and is controlled by the microprocessor, amplifying, rectifying and filtering units controlled by the microprocessor, and an indicator and/or analyzer unit connected to the microprocessor for indicating the measurement results.

The device of the invention is used for registering the diameters and/or distributions of the fibre bundles at the head box of the paper machine or in the direction of thickness of the web placed on the forming wire and/or between two forming wires, and/or for registering air bubbles present in the pulp suspension layer or flow, and/or for registering the consistency or variations in the consistency of the pulp suspension layer or flow, and/or as a detector and measurement apparatus in different control systems of a paper machine, and/or as apparatus in research and development work related to paper machines.

In the device of the invention, the prior art piezoelectric crystal shaped like a circular disc is replaced by a concave, focusing ultrasonic crystal, so that the ultrasonic pulse may be directed at a small volume element inside the pulp suspension layer or flow at the desired point, for example, measured from the surface of the wire. Under these circumstances, it is possible, by means of a sufficiently frequently repeated ultrasonic echo sounding, to follow, in detail, the small scale variation in consistency in the pulp layer in a manner similar to the operation of the prior art bottom meter at the point in the pulp determined by the focal distance of the detector crystal. The use of a crystal of a sufficiently high frequency permits the distance of the "focal point" to be made very short, of the order of one wavelength, and permits the frequency of repetition of the sounding to be made sufficiently high, so that the variations in consistency caused even by the smallest fibre bundles or flocs may be registered.

The simultaneous use of several focused ultrasonic detectors of different focal distances permits the web formation process to be followed constantly within the wire part at different points quantitatively at different levels from the bottom surface to the top surface. Since detectors of very short focal distance are presently available, it is also possible to go between the two wires and to utilize the device of the invention to register the formation of the web in twin wire formers up to the "dry line", after which the web contains too much air for the ultrasound to make progress in it.

The information provided by the variations in the echo intensity obtained from the detectors is processed by microprocessors, for example, so that it becomes suitable for different purposes. Thus, for example, the result obtained is relative quantities of different floc sizes in the different layers of the pulp, consistency of the web in its different layers, registration of air bubbles, if any, in different layers, presentation of the results on a TV monitor, which illustrates the web formation process via a multilayer picture.

The most appropriate crystal geometries, frequencies, and transmitter-receiver crystal combinations vary in accordance with the object of application.

The device of the invention provides a picture as complete as possible of the web formation process starting right from the head box, for example, from its slice part, and ending at the "dry" area. In this manner, it is possible, more efficiently than in the prior art, to develop the construction of the wire part of a paper machine in view of optimization of the web formation. The device of the invention may also be used for the adjustment and on-line measurement of different parts of a paper machine.

BRIEF DESCRIPTION OF THE DRAWINGS

For a fuller understanding of the invention, reference is had to the following description, taken in connection with the accompanying drawings, in which.

DESCRIPTION OF PREFERRED EMBODIMENTS

Figure 1:
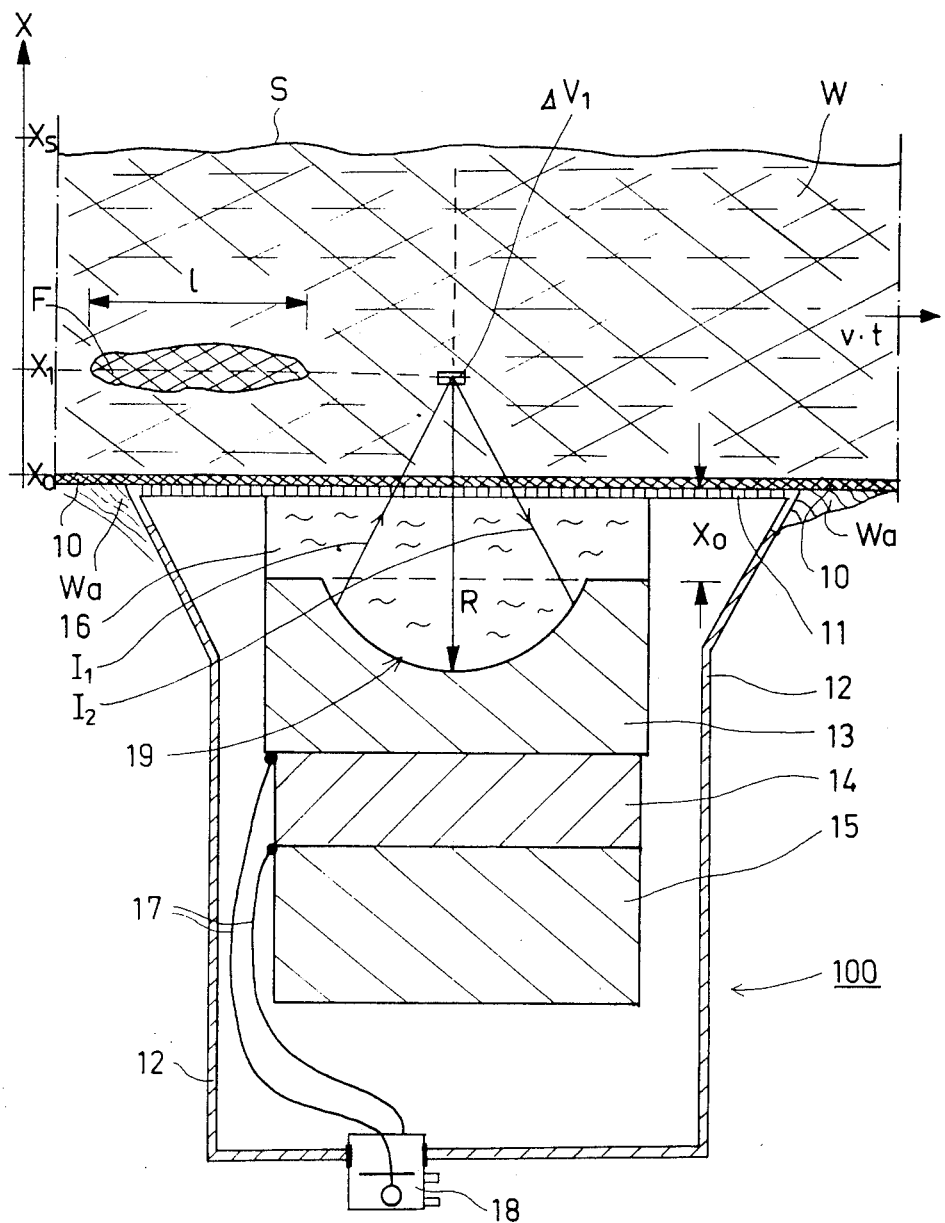
FIG. 1 is a schematic sectional view of an embodiment of a focusing ultrasonic detector of the ultrasonic echo sounding device of the invention.

In FIG. 1, an ultrasonic detector 100 of the invention is connected to a forming wire 10 passing by the detector at a speed v. A pulp suspension layer W having a direction of thickness X is on the wire 10. A paper or board web is formed on the wire 10 from the pulp suspension layer W, in a known manner, as the water is drained through the meshes in the wire 10. The pulp suspension layer W has a top surface S. The pulp suspension layer W contains fibres, additives and filler agents, as well as water.

In the web formation, it commonly occurs that the pulp suspension layer W first starts being couched to a certain extent at the side placed against the wire 10; the water being drained further through the couched layer. "Couching" means that the fibre network is "locked", so that the fibres cannot move relative to each other; at least, not to a significant extent.

The device of the invention, which is described hereinafter in greater detail, includes a focusing ultrasonic detector 100. The ultrasonic detector 100 comprises a conventional piezoelectric crystal 14 and an acoustic lens 13 placed on said crystal. The lens 13 consists of aluminum, for example, having a lens-shaped surface 19, substantially of a shape of a calotte of a sphere, for example. A water space 16, in which the water or any other appropriate liquid, such as, for example, oil, acts as the connecting liquid, is provided above the surface 19. A protective film 11 at the upper side of the detector 100 acts against the lower surface of the forming wire 10. The water Wa drained through the wire 10 acts naturally as a connecting liquid, thereby providing a reliable acoustic connection between the ultrasonic crystal 14 and the pulp suspension layer W.

It is important that the top surface of protective film 11 of the detector 100 be straight and the edges sharp. In this manner, a tight acoustic connection is produced with the wire, and the liquid film, such as, for example, a water film, formed in between acts efficiently. In any case, it is necessary to exclude any passage of air from between the wire 10 and the detector 100, since air destroys the good acoustic connection.

The detector 100 concentrates its ultrasonic pulse on a specific space element $\Delta V_1$, of small dimensions, inside the pulp suspension layer W. In FIG. 1, the space element $\Delta V_1$ is a distance $X_1$ from the plane of the wire 10. The pulp suspension layer W has a thickness $X_s$.

The invention is based on ultrasonic echo sounding and on the use of a series of focusing ultrasonic detectors 100 or acoustic lenses, so that the echo returning to the lens surface 19 is reflected substantially from the very focal points of the lenses 19, that is, from the space element $\Delta V_1$. Information concerning the physical parameters of the space element $\Delta V_1$ is obtained in this manner.

FIG. 1 schematically shows a fibre bundle or floc F at a distance $X_1$ from the wire 10. The floc F has a length 1. When the web W moves at a speed v and passes by the space element $\Delta V_1$, placed at the focus of the ultrasonic detector 100, from the location of the floc, during the time $t_o = 1/v$, a stronger echo is received, on the basis of which the floc, that is, its length 1 and location in the direction of thickness $X_1$, may be detected.

A backing piece 15 is fitted on the opposite side of the piezoelectric crystal 14, relative to the acoustic lens 13. The backing piece 15 attenuates the crystal 14 and makes it aperiodic. Plastic is used as the material of the backing piece 15. A suitable plastic is, for example, ARALDIT (TM) in which tungsten powder has been mixed at an appropriate ratio. In this manner, a strongly attenuating backing is obtained. The detector 100 is placed in a frame box 12 having an electric contact 18, to which conductors 17 connected to the crystal 14 are connected. The lens surface 19 of the acoustic lens 13 has a curve radius R, which determines the location of the focus of said lens in the direction of the x-axis.

In FIG. 1, an arrow $I_1$ illustrates the ultrasonic field emitted from the detector and an arrow $I_2$ shows the echo reflected from the space element $\Delta V_1$. In practice, both the emitted ultrasonic field and the echo are directed at the focus conically, and are reflected from it correspondingly conically onto the lens surface 19. If the lens surface 19 is a spherical surface, the space element $\Delta V_1$ is a small ring or spherical element. It is also possible to use an acoustic lens having the shape of a portion of a circular cylindrical surface, whose focus is correspondingly linear. The lens is preferably perpendicular to the direction of progress vt of the pulp suspension layer W.

The higher the frequency f of the ultrasonic waves used, the shorter the focus and the more accurate the resolution. In practice, the frequency of the ultrasound used in the device of the invention is, as a rule, within the range of $f = 4$ to 20 MHz.

Figure 2:
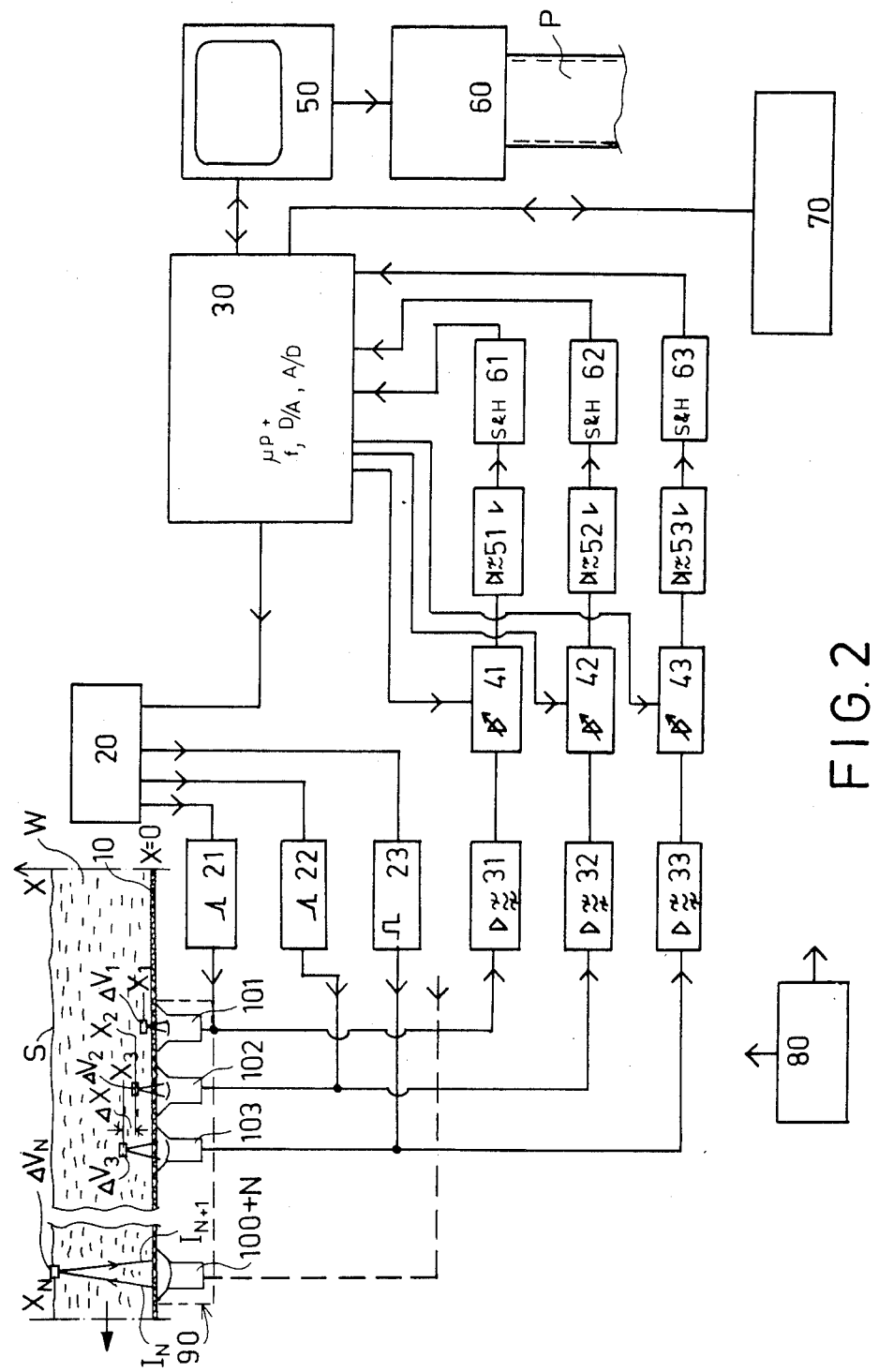
FIG. 2 is a block diagram of an embodiment of the ultrasonic echo sounding device of the invention utilizing a plurality of ultrasonic detectors connected to the wire.

As clarified in the description of FIG. 2, in the device of the invention, a series of ultrasonic detectors 100 have focal distances of different length, which are preferably distributed uniformly spaced over the thickness $X_s$ of the pulp suspension layer W.

Since the layer thicknesses $X_s$ of the pulp suspension W are usually quite short, typically within the range of 2 to 20 mm, for example, the focal distance of the detector 100 must be quite short. However, there may be practical difficulties in making the focal distance $X_1$ very short. For this reason, a water delay is used on the acoustic lens 13,19, as shown in FIG. 1. That is, the water space 16 is placed beneath the protective film 11 and functions to increase the focal distance by a distance $X_o$.

The ultrasonic detector 100 may be similar to that described in a paper entitled, "Elastic Constants Measurement in the Acoustic Microscope", by D. A. Sinclair, I. R. Smith and H. K. Wickrasmasinghe, IEEE, 1982, Ultrasonics Symposium, San Diego, Proceedings, Vol. 2, pages 644 to 649.

The following description of FIG. 2 is of the overall implementation of the device of the invention, including the electronics.

As shown in FIG. 2, N ultrasonic crystals 100 are connected to the wire 10 in its running direction, either sequentially or side by side, or both. The device of FIG. 2 has ultrasonic detectors 101,102,103 ... 100+N. Each ultrasonic detector, comprising a crystal, is thus a transducer. Each crystal 101 to 100+N has its own focal point at different distances $X_N$ in the direction of the thickness X of the pulp suspension layer W. The detector 101 has a focal distance $X_1$, the detector 102 has a focal distance $X_2$, the detector 103 has a focal distance $X_3$, and the detector 100+N has a focal distance $X_N$.

The focal distance $X_1$ of the first detector 101 is near the wire 10, whereas the focal distance of the last detector 100+N is at or near the top surface S of the pulp suspension layer W. In this manner, in accordance with the invention, the space elements $\Delta V_1$, $\Delta V_2$, $\Delta V_3$ ... $\Delta V_N$ to be studied, on which the focal points of the detectors 101 to 100+N are concentrated, may be positioned at sufficiently short stepped spaces $\Delta X$ in the direction of thickness X of the pulp suspension layer W. Thus, in accordance with the invention, the pulp suspension layer W may be echo-sounded via ultrasonics per the principle of multilayer radiography.

The ultrasonic detectors 101 to 100+N are fitted on a frame 90, positioned beneath the wire 10. The frame 90 may be arranged so that it extends in the transverse direction of the paper machine, so that information and the registration of parameters related to the web are also obtained in the transverse direction of the pulp suspension layer W and the wire 10.

A plurality of series of detectors 101 to 100+N may be placed side by side and observations may be made by going through each series of detectors, in sequence, with time.

As shown in FIG. 2, the electronics of the device of the invention includes a microprocessor 30, which performs a major part of the functions related to the operation and control of said device. The microprocessor 30 controls a sequence generator 20 via its basic frequency, and said sequence generator controls N pulse generators 21,22,23, ... connected as shown in FIG. 2, so that they operate sequentially. The pulse generators 21,22,23, ... apply pulses to the ultrasonic detectors 101 to 100+N. The echo pulses obtained from the detectors 101 to 100+N are applied to N pre-amplifiers 31, 32,33, ... Each detector is thus also a transceiver, since it transmits and receives pulses. In the pre-amplifiers 31,32,33, ... the echo pulse signals are amplified and passed to time-controlled amplifiers 41,42,43, ..., which are controlled by the microprocessor 30. The outputs of the amplifiers 41,42,43, ... are connected to blocks 51,52,53, ..., each of which includes a rectifier, a low-pass filter and an amplifier. The outputs of the blocks 51,52,53, ... are connected to the inputs of blocks 61,62,63, ..., each of which is a sample and hold amplifier. The outputs of the sample and hold amplifiers 61,62,63, ... are connected to the microprocessor 30.

The microprocessor 30 includes the necessary interfaces, that is, inputs and outputs, as well as D/A and A/D converters. The microprocessor 30 is connected to a monitor 50, which converts received information to an optically observable form. The monitor 50 is connected to a printer 60 or equivalent, which provides an appropriate print P of the parameters detected. The microprocessor 30 is connected to an FFT, or Fast Fourier Transform, processor and to a frequency analyzer 70 which analyzes the floc size. The device includes a power supply unit 80.

In the embodiment of FIG. 2, each of the series of detectors 101 to 100+N of detectors 100 has a focal distance $X_1$ to $X_N$ of its own. The device of the invention may, however, utilize an acoustic lens arrangement similar to the Fresnel lens, known in optics. The lens arrangement has coaxial concave ring surfaces, each of which has a focal distance of its own, that is, individual focusing points are provided.

The device of the invention may also utilize the correlation technique, as described, for example, in Finnish patent application No. 81-3259 of Eino Harkonen. The echo-sounding device of the Finnish application measures the speed of the pulp suspension flow in the distribution pipe system of the head box of a paper machine, for example, although a corresponding correlation technique may also be utilized in the device of the invention.

The device of the invention may also be used in the head box of a paper machine, in its slice cone, for example, for observation of variations in consistency and/or turbulence in the pulp suspension flow. To accomplish this, a series of detectors in accordance with the invention, or several series of detectors placed side by side in the transverse direction of the paper machine, are connected to the wall of the slice cone portion. A series of focused ultrasonic pulses are directed from the detectors in the transverse direction of the pulp suspension flow, preferably evenly spaced, in accordance with the aforedescribed principles. The device of the invention may also be used in other pulp suspension flow channels in the head box such as, for example, the distributor roll, the distributor pipe system, the equalizing chamber, and/or the turbulence generator, especially in research and development work on the head box.

As explained in connection with FIG. 1, the size of the flocs, which is the length l of the floc F in FIG. 1, may be registered on the basis of the duration $T_o$ of the echo signal produced by the floc. The basic principle is that the more fibres there are in a space element $\Delta V$ at the focus of the detector 100, the higher the intensity of the ultrasonic echo. The integral of the echo signals illustrates the consistency, because the integration time, that is, the measurement time of the emitted pulse and echo pulse of each detector 100, is quite short.

The device of the invention may also function to detect the number, size and distribution of air bubbles present in the pulp suspension layer W. This information is important for the papermaker in practice. It is possible to calculate the air content of the pulp suspension layer W from such information. The air bubbles generally have a diameter of the order of about 0.1 mm. Thus, the resolution of the device of the invention is also adequate for detecting the air bubbles. The device of the invention is thus an important tool for development work on paper machine.

The device of the invention may be used as a component of closed control systems of a paper machine. Such device permits control of the quantity of retention agents, adjustment of the dewatering at the forming board and adjustment of the feed angles of the head box as well as the overall consistency of the pulp. When the device of the invention is utilized with twin wire sections, it is possible to control the dewatering in different directions, since information is obtained concerning the distribution of the consistency in the direction of thickness X of the pulp suspension layer W.

Each series of ultrasonic detectors includes several detectors 100. The number N of detectors is generally within the range of 5 to 20, preferably 10.

The time T of one measurement sequence, that is, the time taken for one sounding, is of the order of $10^{-3}$ to $10^{-5}$ s. The dimensions of the volume element V at the focal points of the acoustic lenses are of the order of the wavelength used. If the frequency of the ultrasound used is about 10 MHz, this corresponds to a resolution of about 0.1 mm, so that it is possible to detect even the smallest fibre bundles or flocs. The resolution of the floc meter known in the art is of the order of 0.2 mm, and it has also been possible to determine the wire marking via such floc meter.

In another embodiment of the invention, the series of detectors fixed focal lengths are replaced by a detector which may be moved periodically relative to the plane of the wire and in which the distance of the focal point from the surface of the wire, that is, in the direction of thickness of the pulp layer, may be adjusted. This adjustment may be accomplished in practice, so that the height of the contact liquid column between the detector and the wire is adjusted by lowering or raising the detector in a cylinder surrounding it by use of an appropriate oscillation mechanism. The mechanical shifting of the crystal may be replaced by using a stationary crystal which is arranged, in a known manner, to be electronically focusable for the purpose of examination of different points in the pulp suspension layers.

The invention is by no means restricted to the aforementioned details which are described only as examples; they may vary within the framework of the invention, as defined in the following claims.

It will thus be seen that the objects set forth above, among those made apparent from the preceding description, are efficiently attained and, since certain changes may be made in the above constructions without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A device for ultrasonic echo sounding for observation of the web formation, the pulp suspension flow on the wire part, and the head box of a paper machine, said device comprising a series of ultrasonic transceivers connected to the wall of the flow channel in the head box or to the forming wire or wires, said transceivers directing an ultrasonic field at the pulp suspension layer and detecting echo signals received from said pulp suspension layer, said transceivers operating as shaped acoustic transceivers, each having a focal point extending in the transverse direction of said pulp suspension flow and in the direction of thickness of said pulp suspension layer in a manner whereby information is provided concerning fibre bundles, air bubbles, variations in consistency, and concerning parameters of said fibre bundles, air bubbles and variations in consistency and their variations in the substantially transverse direction of said pulp suspension flow and in the direction of thickness of said pulp suspension layer.

2. A device as claimed in claim 1, wherein there are 5 to 20 transceivers in said series of transceivers.

3. A device as claimed in claim 1, wherein there are approximately 10 transceivers in said series of transceivers.

4. A device as claimed in claim 1, wherein each of the transceivers of said series of transceivers has a different focal length than the others.

5. A device as claimed in claim 1, wherein the frequency range of the ultrasound in 4 MHz to 20 MHz.

6. A device as claimed in claim 1, wherein each of the transceivers of said series of transceivers includes a focusing piezoelectric crystal for generating an ultrasonic field, the crystal of each of said transceivers being positioned to operate both as a transmitter and receiver of the ultrasonic echo reflected from said pulp suspension flow and from said pulp suspension layer.

7. A device as claimed in claim 1, wherein each of the transceivers of said series of transceivers has a focal distance of its own, the focal distances of said transceivers being evenly spaced in the direction of thickness of said pulp suspension layer, for echo sounding of said pulp suspension layer.

8. A device as claimed in claim 1, wherein each of the transceivers of said series of transceivers has a focal point extending in the direction of thickness of said pulp suspension layer, and further comprising means for adjusting the focal points of said transceivers.

9. A device as claimed in claim 8, wherein said means for adjusting said focal points comprises mechanical means for periodically changing the position of each of said transceivers.

10. A device as claimed in claim 8, wherein said means for adjusting said focal points comprises electronic means for varying the focal distances of said transceivers.

11. An ultrasonic echo sounding device, comprising
a series of ultrasonic transceivers in operative proximity with a web and a pulp suspension layer of a paper machine, each having a different focal length from the others;
A plurality of pulse generators each connected to a corresponding one of said transceivers;
a microprocessor;
a sequence generator connected to said transceivers and to said microprocessor, said sequence generator controlling said pulse generators and said microprocessor controlling said sequence generator;
a plurality of amplifying, rectifying and filtering units connected between said microprocessor and said transceivers, said microprocessor controlling said amplifying, rectifying and filtering units; and
indicating and analyzing means connected to said microprocessor, said indicating and analyzing means indicating formation of said web and pulp suspension flow of said pulp suspension layer.

12. A device as claimed in claim 11, wherein each of said ultrasonic transceivers has a piezoelectric crystal with opposite sides, an acoustic lens having a concave lens surface and a specific focal distance at one side of said crystal and a backing piece at the opposite side of said crystal for attenuating said crystal so that it becomes aperiodic.

13. A device as claimed in claim 12, further comprising a plurality of frame boxes, each of said transceivers being in a corresponding one of said frame boxes, a protective film on a selected surface of each of said frame boxes positioned against the inside surface of the forming wire whereby water drained through said forming wire acts as an acoustic connecting liquid.

14. A device as claimed in claim 13, further comprising a liquid space on the lens surface of the acoustic lens of each of said crystals for increasing the focal distance, focused ultrasonic pulses and echo signals passing through said liquid space to and from said lens surface.

15. A device as claimed in claim 14, wherein each of said transceivers has a focal point and focal distance extending in the direction of thickness of said pulp suspension layer, and further comprising means for adjusting the focal points of said transceivers.

16. A device as claimed in claim 15, wherein said means for adjusting said focal points comprises mechanical means for periodically changing the position of each of said transceivers.

17. A device as claimed in claim 15, wherein said means for adjusting said focal points comprises electronic means for varying the focal distances of said transceivers.

18. A device as claimed in claim 15, wherein said means for adjusting said focal points also adjusts the thickness of said liquid space and also changes said thickness periodically.

19. A device as claimed in claim 15, wherein said indicating and analyzing means indicate the diameters and distributions of the fibre bundles at the head box of the paper machine and in the direction of thickness of the web placed on the forming wire and/or between two forming wires, indicate air bubbles present in said pulp suspension layer, and indicate consistency and variations in consistency of said pulp suspension layer and said pulp suspension flow.

20. A method of ultrasonic echo sounding for observation of the web formation, the pulp suspension flow on the wire part, and the headbox of a paper machine, said method utilizing ultrasonic transceivers, said method comprising the steps of directing an ultrasonic field from the ultrasonic transceivers at the pulp suspension layer;

detecting at the ultrasonic transceivers echo signals received from said pulp suspension layer; and operating said transceivers as shaped acoustic transceivers to provide a focal point for each of said transceivers extending in the transverse direction of said pulp suspension flow and in the direction of thickness of said pulp suspension layer in a manner whereby information is provided concerning fibre bundles, air bubbles, variations in consistence, and concerning parameters of said fibre bundles, air bubbles and variations in consistency and their variations in the substantially transverse direction of said pulp suspension flow and in the direction of thickness of said pulp suspension layer.

21. A method as claimed in claim 20, wherein each of said transceivers is provided with a different focal length than the others.

22. A method as claimed in claim 20, wherein each of said transceivers is provided with a focal point extending in the direction of thickness of said pulp suspension layer, and further comprising the step of adjusting the focal points of said transceivers.

* * * * *